US00PP11517P

United States Patent [19]

Carruth

[11] Patent Number: Plant 11,517

[45] Date of Patent: Sep. 26, 2000

[54] FLORIBUNDA ROSE PLANT NAMED 'WEKPLAPIC'

[75] Inventor: Thomas F. Carruth, Altadena, Calif.

[73] Assignee: Weeks Wholesale Rose Grower, Inc., Upland, Calif.

[21] Appl. No.: 09/198,228

[22] Filed: Nov. 23, 1998

[51] Int. Cl.[7] ..... A01H 5/00

[52] U.S. Cl. ..... Plt./143

[58] Field of Search ..... Plt./141, 142, 143, Plt./102

*Primary Examiner*—Howard J. Locker

*Attorney, Agent, or Firm*—Christie, Parker & Hale, LLP

[57] ABSTRACT

A new variety of Floribunda rose suitable for garden decoration, having semi-double flowers of ivory edged red coloration.

1 Drawing Sheet

BACKGROUND OF THE INVENTION

This invention relates to a new and distinct variety of Floribunda Rose. The varietal denomination of the new variety is 'WEKplapic'. It has as its seed parent the variety known as Playboy and as its pollen parent the variety known as 'MACpic' (U.S. Plant Pat. No. 3,351).

SUMMARY OF THE INVENTION

Among the features which distinguish the new variety from other presently available and known commercial rose cultivars are the following combination of characteristics: its undulated semi-double flowers with strongly bordered coloration, its dark red new growth, its dark coloration of the stamens, its inability to set hips and its very short time between bloom cycles. The plant is a bushy upright growing plant, suitable for outdoor garden decoration.

Asexual reproduction of the new variety by budding as performed in Kern County and Upland, Calif., shows that the foregoing and other distinguishing characteristics come true to form and are established and transmitted through succeeding propagations. 'WEKplapic' may be asexually propagated by cuttings, budding or grafting.

COMPARISON WITH PARENTS

The new rose may be distinguished from its seed parent, 'Playboy', by the following combination of characteristics: whereas 'WEKplapic' bears ivory yellow flowers with a red border, 'Playboy' bears flowers of yellow blushed with orange. The seed parent will readily set hips in the Upland, Calif. growing conditions, whereas the new seedling does not set hips. 'Playboy' bears flowers with bright yellow stamens, whereas 'WEKplapic' bears flowers with stamens of significantly darker coloration.

The new variety may be distingushed from its pollen parent, 'MACpic', by the following combination of characteristics: whereas 'WEKplapic' bears ivory yellow flowers with a red border, 'Macpic' bears flowers of scarlet reversed and marked with white. The pollen parent bears flowers with 15 to 18 petals, whereas the new seedling bears flowers of significantly lesser petalage (about 9 to about 12).

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of October. Phenotypic expression may vary with environmental, cultural and climatic conditions, as well as differences in conditions of light and soil.

FLOWER

The new variety sometimes bears its flowers singly, usually in clusters of four to five or more per stem. Flowers are borne in irregular rounded clusters on normal strong short to medium length stems (about 16 to about 22 cms.). Outdoors, the plant blooms very abundantly and nearly continuously during the growing season. The flowers have a slight tea fragrance.

BUD

The peduncle is about 3.5 to about 5.5 cms. in length, of average to heavy caliper, and usually erect. It is moderately smooth, with many stipitate glands and few hairs. Peduncle color is between 144A and 137C, sometimes moderately blushed on the side exposed to the sun with between 183B and 178A.

Before the calyx breaks, the bud is about 1.2 to about 1.6 cms. in diameter at the widest point, about 1.7 to about 2.5 cms. in length, and very pointed to ovoid in shape with a conspicuous hypanthium. The surface of the bud bears few stipitate glands and hairs, usually with slender entire foliaceous parts extending beyond the tip of the bud about ¼ or more of its length. Bud color is between 144A and 137C, sometimes moderately blushed on the side exposed to the sun with between 183B and 178A.

The inner surface of the sepals is covered with fine wooly tomentum; sepal margins are lined with many stipitate glands and hairs, sometimes bearing one to two or more moderately small slender foliaceous parts.

As the petals open (after the calyx breaks), the bud is about 1.7 to about 2.2 cms. in diameter at the widest point, about 2.4 to about 2.8 cms. in length, and very pointed to ovoid in form. The color of the under surfaces of the newly opened petals is between 13B and 15C, usually blushed on areas exposed to the sun with as dark as between 53B and 46A. At the point where the petal attaches, there is a moderately small zone of near 7B. The color of the interior portion of the upper surfaces of the newly opened petals is between 13B and 15C suffusing to a broad edging of between 45A and 46A. At the point where the petal attaches, there is a moderately small zone of near 7A.

BLOOM

When fully open, the bloom ranges from about 7 to about 9 cms. in diameter. Petalage is semi-double with about 9 to 12 petals and about 1 to 3 petaloids arranged irregularly. When partially open, the bloom form is moderately high centered and the petals are loosely spiraled with petal edges slightly reflexed outward. When fully open, the bloom form is more flat to cupped and the petals are somewhat cupped to moderately undulated with petal edges somewhat reflexed outward.

PETALS

The substance of the petals is moderately heavy and of medium to thick thickness, with upper surfaces very satiny to somewhat velvety and under surfaces moderately shiny to satiny. The petals are nearly round to broadly obovate in shape with apices usually rounded to sometimes mucronate.

NEWLY OPENED FLOWER

The color of the interior portion of the under surface of the petals is between 13C and 15D suffusing slowly to a moderately sized edging of between 53B and 46B. At the point where the petal attaches, there is a moderately small zone of near 7C. The color of the interior portion of the upper surface of the petals is between 13C and 15D suffusing to a broad edging of between 53B and 46A. At the point where the petal attaches, there is a moderatlely small zone of near 7A.

The general tonality of the newly opened flower is between 13C and 15D broadly edged with between 53B and 46A.

THREE DAY OLD FLOWER

The color of the interior portion of the under surface of the petals is between 19D and 11D suffusing very slowly to a moderately thin edging of between 53B and 53C. At the point where the petal attaches, there is a very small zone of near 8C. The color of the interior portion of the upper surface of the petals is between 155B and 49D suffusing gradually to a very broad edging of as deep as between 53B and 53C. At the point where the petal attaches, there is a moderately small zone of near 8B.

The general tonality of the three day old flower is between 155B and 49D very broadly edged with as deep as between 53B and 53C.

On the spent bloom, the petals eventually drop off cleanly after fading to between 155B and lighter than 49D edged with between 53C and 53D.

In October in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are average to many in number (approximately 75) and are arranged regularly about the pistil. The filaments are of moderately long length, most with anthers. Filaments are between 14A and 15A in color. The anthers are medium sized and all open approximately at the same time. Anther color is between 17A and 163A when immature and between 165A and 166A at maturity. Pollen is somewhat sparse near 16C in color.

FEMALE REPRODUCTIVE ORGANS

Pistils vary in number (approximately 45). The styles are moderately short to somewhat uneven, somewhat thin to average in caliper, and very bunched. Stigma and style color is near 4B. Ovaries are usually all enclosed in the calyx.

Hips will not set on this variety under Upland, Calif. growing conditions.

FOLIAGE

The compound leaves are usually comprised of three to five leaflets and are borne abundantly. The leaves are about 9 to about 12 cms. in length and about 7 to about 10 cms. in width at the widest point, moderately heavy in texture, and very glossy in finish. The leaflets are about 4.5 to about 8 cms. in length and about 3 to about 5 cms. in width at the widest point, shaped oval to somewhat ovate with acute apices and bases. Their margins are usually simply serrate.

The upper surface of the mature leaf is between 137A and 139A. The under surface of the mature leaf is between 147B and 147C. The upper surface of the young leaf is between 144A and 137C usually heavily suffused with between 187A and 183A. The under surface of the young leaf is between 144B and 138B usually moderately suffused with near 183B.

The rachis average in caliper and somewhat smooth. The upper side is moderately grooved with some stipitate glands on the edges of the grooves. The upper side is sometimes suffused with near 183B. The under side of the rachis is moderately smooth with a few stipitate glands, sometimes with about one or two very small prickles.

The stipules are about 0.7 to about 1.2 cms. in length and moderately narrow width medium long straight points that usually turn out in an angle of more than 45 degrees.

The plant displays an above average degree of resistance to powdery mildew and blackspot as compared to other commercial varieties grown under comparable conditions in Upland, Calif.

GROWTH

The plant has a bushy upright medium height growth habit (about 90 to about 140 cms. in height and about 105 to about 130 cms. spread at the widest point) with very full branching. It displays very vigorous growth and the canes are of somewhat light to medium caliper for the class.

The color of the major stems is between 146C and 144B. They bear very few large prickles which are about 0.8 to about 1.3 cms. in length. The large prickles are almost straight, angled slightly downward with a medium length moderately narrow base; prickle color is near 164A. The major stem bears very few small prickles of similar shape and coloration.

The color of the branches is between 146B and 144A often moderately suffused with between 178A and 183D. They bear few large prickles, which are of similar size and shape to the large prickles on the major stems; prickle color is between 176D and 181C. The branches bear very few small prickles of similar shape and coloration.

The color of the new shoots is near 144A usually heavily suffused with between 183A and 187B. They bear few large prickles, which are of similar size and shape to the large prickles on the major stems; prickle color is between 178A and 183B. The shoots bear few small prickles of similar shape and coloration.

I claim:

1. A new and distinct Floribunda rose plant of the variety substantially as described and illustrated herein.

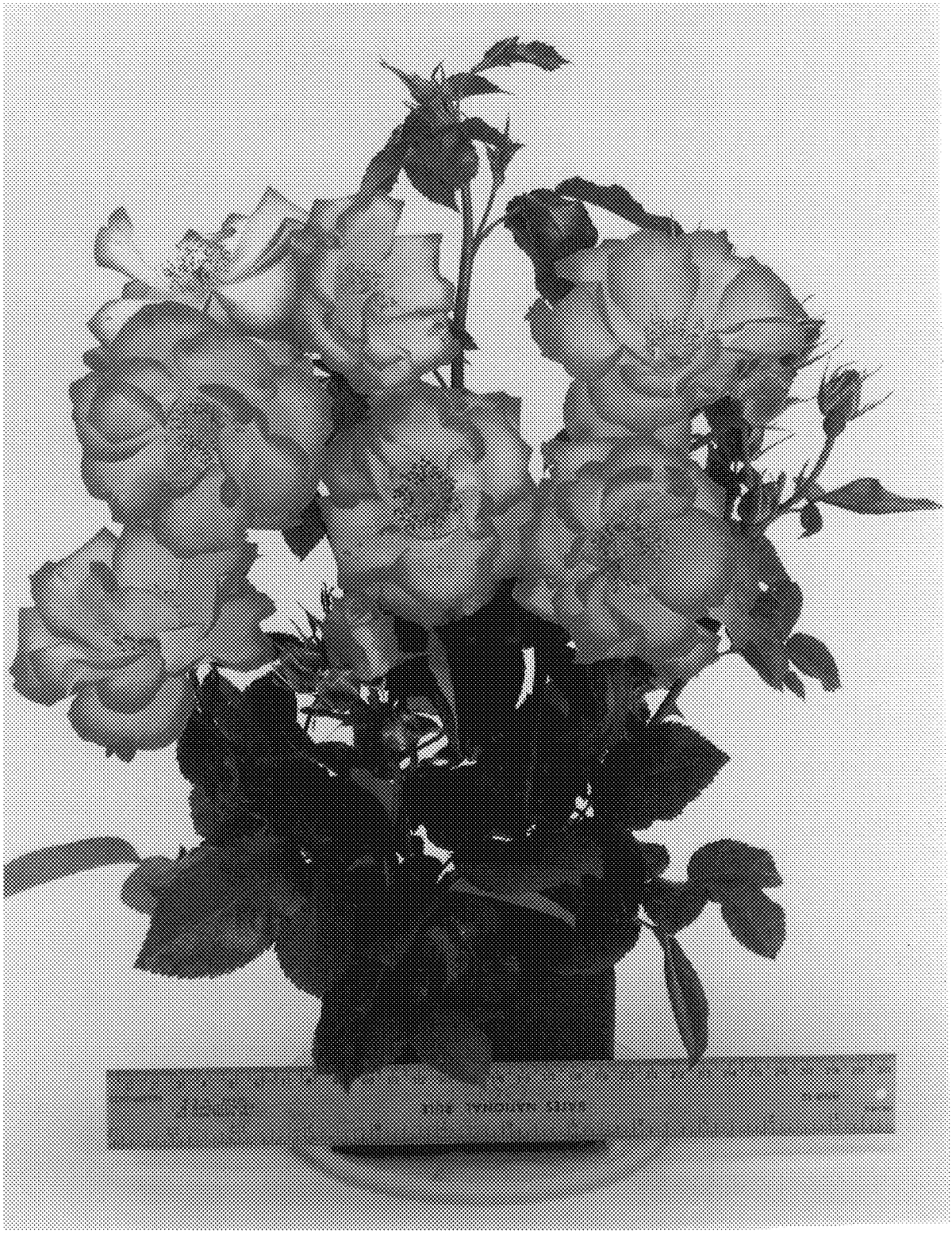

* * * * *